Feb. 23, 1954 W. E. LAMMERTS Plant Pat. 1,259
ROSE PLANT
Filed March 9, 1953
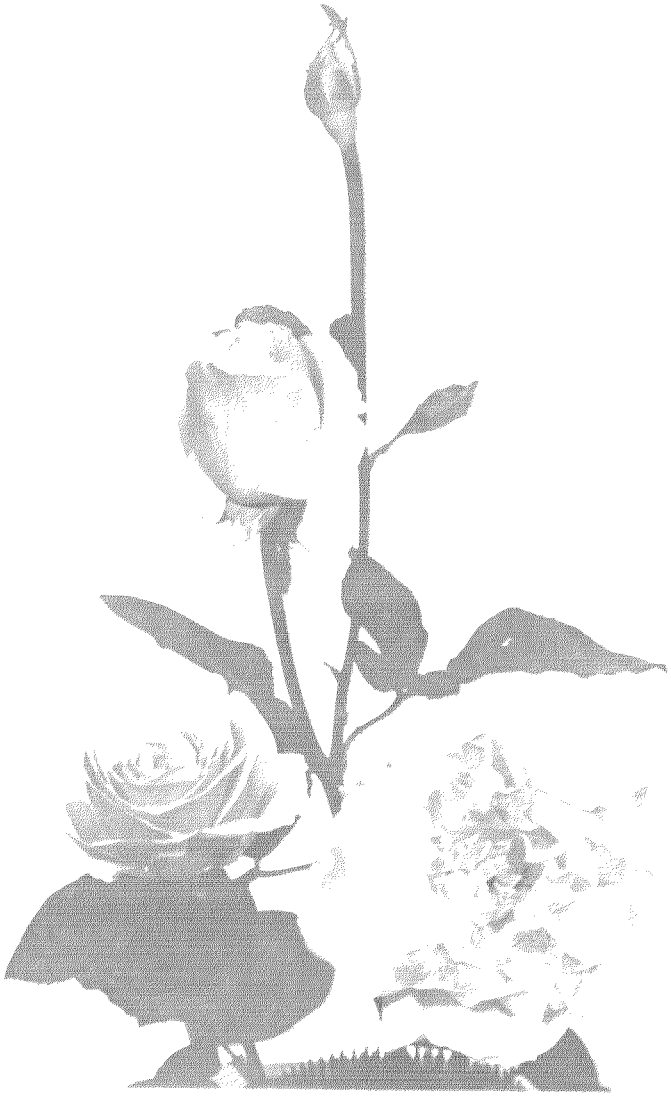
Inventor
W. E. Lammerts
By: Robert Cobb
Attorney.

Patented Feb. 23, 1954 Plant Pat. 1,259

UNITED STATES PATENT OFFICE 1,259

ROSE PLANT

Walter E. Lammerts, La Canada, Calif., assignor, by mesne assignments, to Germain's, Inc., Van Nuys, Calif., a corporation of California Application March 9, 1953, Serial No. 341,385

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Floradora" (unpatented).

As the result of this cross, I have produced a new variety of rose which is primarily characterized by a unique combination of unusual vigor and upright growth, large, leathery and glossy dark green leaves which abundantly clothe the plant, a distinctive tinge of Garnet Brown color in the young shoots, and the Pansy Purple tinge of the young foliage which make the new growth of the plant especially attractive. The foregoing characteristics are still further combined with distinctive characteristics of the blooms of my new variety, said blooms being borne very abundantly on relatively long, cutting stems, thus combining the floriferousness of the parent variety "Floradora" with the good cutting stem and bud form which is characteristic of the parent "Charlotte Armstrong."

A still further important characteristic of my new variety is the unusually clear Carmine Rose to Dawn Pink general color tonality of the flowers, and their unique fading reaction which in the final stage runs to lighter shades of Carmine Rose to Dawn Pink, with the outer ¼ of the petals heavily peppered with Carmine, particularly where the sun strikes the blooms most strongly. This unique final coloring is fully as attractive as the opening color, although distinctively different from the latter.

Asexual reproduction of my new variety by budding at La Canada, California, shows that the foregoing characteristics and distinctions come true to form and are established and transmitted through succeeding propagations.

The accompanying drawing shows typical specimens of the flowers, foliage and stems of my new variety in different stages of development.

The following is a detailed description of my new variety, with color terminology in accordance with the Horticultural Color Chart of the British Color Council, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Charlotte Armstrong."
*Pollen parent.*—"Floradora."
Propagation: Holds its distinguishing characteristics through succeeding propagations by budding.

*Flower*

Locality where grown and observed: La Canada, California.
Flowers borne: Usually singly, but occasionally 2 or 3 to stem; on strong, long stems.
Quantity of bloom: Abundant, outdoors.
Continuity: Continuous.
Fragrance: Moderate; centifolia.
Bud:
*Peduncle.*—Medium length; heavy; erect; stiff; entirely smooth; few gland-tipped hairs, but no prickles or thorns. Color—greenish bronze.
*Before calyx breaks.* — Size — medium. Form—medium length; pointed; with foliaceous appendages on the edges of alternate sepals varying from ⅛ inch to ⅜ inch long by $\frac{1}{16}$ inch to ⅛ inch wide, said appendages being lance-shaped. Color—from Carmine, Plate 21, to Carmine, Plate 21/1.
*As calyx breaks.*—Color—general color Carmine, Plate 21/2, with streak of China Rose, plate 024 near midrib.
*As first petal opens.*—Size—medium. Form—pointed. Color: outside—Crimson, Plate 22/2, shading to Neyron Rose, Plate 623/1; inside—Carmine Rose, Plate 621/2.
*Opening.*—Opens up well.
Bloom:
*Size, when fully open.*—3½ inches to 4 inches.
*Petalage.*—From 37 to 40 petals; arranged regularly.
*Form.*—Very high center at first; becoming cupped; petals being at first rolled inward; becoming later at maturity loosely rolled outward; very regularly imbricate petal arrangement, with inner petals and petaloids rolled inward and covering stamens.
Petals: Medium thin, with both inside and outside satiny. Shape: outside—obovate, with apex $\frac{1}{16}$ inch long; no notches; intermediate—obovate; usually with 1 notch, but occasionally some with short apex.

This description of a newly opened flower was made from a rose grown outdoors in the month of October, at La Canada, California:

*Color.*—Outside petal: outside surface—Neyron Rose, Plate 623/1; inside surface—Carmine Rose, Plate 621/2. Intermediate petal: outside surface—Neyron Rose, Plate 623/2; inside surface—Dawn Pink, Plate 523/1. Inner petal: outside surface—

Neyron Rose, Plate 623/2; inside surface—Dawn Pink, Plate 523/2.

This description was made from a rose that was open for 3 days outdoors in the month of October, at La Canada, California:

*Color.*—Outside petal: outside surface—Neyron Rose, Plate 623/2; inside surface—Carmine Rose, Plate 621/3. Inside petal: outside surface—Neyron Rose, Plate 623/3; inside surface—Dawn Pink, Plate 523/3 at base, but peppered with Carmine, Plate 21/2 on outer margin where sun strikes strongest.

*General color effect.*—Newly opened flower—Carmine Rose to Dawn Pink. 3 days open—lighter shades of Carmine Rose to Dawn Pink and strongly influenced by peppered effect of Carmine on outer part of petals.

*Behavior.*—Drop off cleanly; affected very little by heat or cold.

*Longevity.*—One bush in garden—5 days in October. Cut roses grown outdoors and kept at livingroom temperature—6 days in October.

*Reproductive organs*

Stamens: Medium number; arranged irregularly about pistils.

Filaments: Some short, but mostly medium length; most with anthers. Color—French Rose, Plate 520.

Anthers: Medium size; open at various times. Color—Majolica Yellow, Plate 09.

Pollen: Moderate. Color—gold.

Pistils: Medium number.

Styles: Uneven; medium length; medium caliper; bunched. Color—upper part Claret Rose, Plate 021.

Stigma: Color—yellow.

Ovaries: All enclosed in calyx.

Hips: Globular; with inconspicuous neck; smooth; walls thin. Color—yellow.

Sepals: Falling soon; recurved. Color—Willow Green, Plate 000862/2.

*Plant*

Foliage:

*Leaves.*—Compound of 5 to 7 leaflets; abundant; moderately large; heavy; leathery; glossy.

*Leaflets.*—Shape—elliptical, with round base. Margin—simply serrate.

*Color.*—Mature: upper surface—nearly Parsley Green, Plate 00962; under surface—nearly Spinach Green, Plate 0960/3. Young: upper surface—Parsley Green, Plate 00962/1 at base, tinged with Pansy Purple, Plate 928; under surface—Spinach Green, Plate 0960/2, strongly tinged with Pansy Purple, Plate 928.

*Rachis (the supporting stem of the compound leaf.)* — Heavy. Upper side — smooth; grooved. Under side—smooth, but occasionally with one small thorn at each leaf junction and occasionally between leaf junctions.

*Stipules.*—Short; narrow; with short points turning out at an angle of 45°.

*Disease.*—Resistant to mildew, as determined by comparison with susceptible varieties grown nearby under comparable cultural conditions and which were heavily infested with mildew.

Growth:

*Habit.*—Bushy; upright.

*Growth.*—Very vigorous.

*Canes.*—Heavy.

*Main stems.*—Color—Parsley Green, Plate 00962/3. Thorns — several; medium length; with long, narrow base. Prickles—none. Hairs—none.

*Branches.* — Color — Parsley Green, Plate 00962/2. Thorns — several; medium length; straight; with long, narrow ovate base. Prickles—none. Hairs—none.

*New shoots.*—Color—Spinach Green, Plate 0960/2, overlaid Garnet Brown, Plate 00918. Thorns—several; medium length; straight; with long, narrow base. Prickles—none. Hairs—none.

I claim:

A new and distinct variety of rose plant of the hybrid tea class, substantially as herein shown and described, characterized particularly as to novelty by its unusual vigor and upright habit of growth, by its large, leathery, glossy dark green leaves and the abundance thereof, by the distinctive heavy tinge of Garnet Brown color in the young shoots, by the Pansy Purple color tinge of the young foliage, by its good cutting stems and good bud form, by its abundant production of flowers borne on relatively long cutting stems, by the unusually clear Carmine Rose to Dawn Pink general color tonality of its flowers, and by the unique fading reaction of the flowers to lighter shades of Carmine Rose to Dawn Pink with the outer portions of the petals becoming heavily peppered with Carmine where sunlight strikes strongest.

WALTER E. LAMMERTS.

No references cited.